(12) United States Patent
Howard

(10) Patent No.: US 7,563,271 B2
(45) Date of Patent: Jul. 21, 2009

(54) BREATHING AID DEVICE THAT DECREASES INCIDENCE OF SNORING

(76) Inventor: Laurence E. Howard, 1250 NE. Lincoln Rd., Poulsbo, WA (US) 98370

( * ) Notice: Subject to any disclaimer, the term of this patent is extended or adjusted under 35 U.S.C. 154(b) by 0 days.

(21) Appl. No.: 11/968,569

(22) Filed: Jan. 2, 2008

(65) Prior Publication Data

US 2008/0167676 A1 Jul. 10, 2008

Related U.S. Application Data

(60) Provisional application No. 60/883,365, filed on Jan. 4, 2007.

(51) Int. Cl.
*A61M 29/00* (2006.01)
(52) U.S. Cl. ..................... 606/199
(58) Field of Classification Search .......... 606/151, 606/199; 128/206.11, 207.18; 24/625, 626
See application file for complete search history.

(56) References Cited

U.S. PATENT DOCUMENTS

| 567,528 | A | * | 9/1896 | Weber ................... 24/626 |
| 1,069,459 | A | * | 8/1913 | Myles ................... 606/199 |
| 1,077,574 | A | | 11/1913 | Woodward |
| 1,481,581 | A | * | 1/1924 | Woodward ............. 606/199 |
| 2,515,756 | A | | 7/1950 | Bove |
| 2,672,138 | A | | 3/1954 | Carlock |
| 3,710,799 | A | | 1/1973 | Caballero |
| D325,439 | S | | 4/1992 | Apple et al. |
| 5,931,852 | A | * | 8/1999 | Brennan ................ 606/199 |
| 6,238,411 | B1 | | 5/2001 | Thorner |
| 6,270,512 | B1 | | 8/2001 | Rittmann |
| 6,863,066 | B2 | | 3/2005 | Ogle |
| 2003/0181941 | A1 | | 9/2003 | Bruggisser et al. |
| 2006/0185676 | A1 | * | 8/2006 | Brown ................ 128/207.18 |
| 2006/0259065 | A1 | * | 11/2006 | Maryanka ............. 606/199 |
| 2006/0266367 | A1 | | 11/2006 | Noce |
| 2007/0062538 | A1 | | 3/2007 | Foggia et al. |

FOREIGN PATENT DOCUMENTS

DE 29718838 U1 5/1998

* cited by examiner

*Primary Examiner*—Todd E Manahan
*Assistant Examiner*—Eric Blatt
(74) *Attorney, Agent, or Firm*—Innovation Law Group, Ltd.; Jacques M. Dulin, Esq.

(57) ABSTRACT

An improved, preferably plastic, universal breathing aid device for insertion into the nasal passages having a first pair of septum-engaging and gripping arms, from which are cantilevered a pair of curved, spring-action nostril-expanding arm that keep the nasal passages open. The septum-engaging arms are supported by a base member in the form of an open loop that includes a living hinge to provide flexibility and accommodation to varying sizes of nasal septums. The flexibility of both sets of arms promotes user comfort. The living hinge urges the septum arms together to provide grip yet comfort via the flexibility of the hinge. The nostril-expanding arms act in the opposite direction, opening the airway. The contours of the arm and tip cross sections may be varied for comfort, and device may range from generally planar to three-dimensional. The inventive device is unobtrusive and easily kept sanitary.

13 Claims, 5 Drawing Sheets

BREATHING AID DEVICE THAT DECREASES INCIDENCE OF SNORING

CROSS REFERENCE TO RELATED APPLICATION

This application is the Regular U.S. application corresponding to related Provisional Application Ser. No. 60/883,365 entitled Breathing Aid Device filed by the same inventor on Jan. 4, 2007, the benefit of the filing date of which is hereby claimed under 35 US Code §119, and other applicable code sections as required, the disclosure of which is hereby incorporated by reference.

FIELD

The invention relates to breathing aid devices and more particularly to universal, plastic devices that are inserted in the nasal passages to compress the septum while holding open the nostrils in order to permit easier breathing and reduce the incidence of obstructed nasal passage-induced snoring.

BACKGROUND

A number of devices have been proposed, patented and offered commercially that are intended to open nasal breathing passageways. These fall in two main classes: A) the externally applied adhesive devices that purport to pull the nostrils open from the exterior; and B) devices that are inserted in the nostrils designed to prop open the nostrils from the interior.

The various prior art devices have been prone to several problems. The external adhesive devices such as "Clear Passage" or "Breathe Right" brand adhesive nasal strips, are generally single-use disposable strips having a thin, planar flexible plastic "spring" member embedded between tape covering, and are claimed to relieve nasal congestion due to allergies or colds and reduce or eliminate snoring. The efficacy of such strips is low in cases of internal nasal tissue deformity or thickening, and depend on proper placement over the bridge of the nose precisely over the obstruction location, which may not be observable. Further, such strips do not adhere for any appreciable length of time, especially during exertion or on the notoriously oily skin of the nose. The user is cautioned to not apply them on irritated or sunburned skin or over sores, and to remove them if skin rashes develop. While stronger adhesives could be used, such adhesives would result in tearing the skin of the user, causing injury and disfigurement. They are also not invisible, and users consider them unsightly.

While various internal, nasal passageway devices have been proposed, such as US patents or Publications: US2003/0181941; U.S. Pat. Nos. 1,077,574; 2,515,756; Des. Pat. No. 325,439; 6,270,512; US2006/0266367; U.S. Pat. No. 6,863,066; US2007/0062538; U.S. Pat. Nos. 6,238,411; 2,672,138; 3,710,799, and DE Patent 297-18-838 U1. Generally, these devices are massive (DE 29718838; US2006/0266367), overly pinch the septum (US2003/0181941), are not fully universal, are uncomfortable, are unsightly or not un-obtrusive (U.S. Pat. Nos. 2,672,138; 6,238,411; 3,710,799; US2006/0266367; DE 2978838), employ cages, tubes or balls that must be stuffed with the fingers up the nasal passages (U.S. Pat. Nos. 3,710,799; 2,672,138; US 2007/006538), and do not fully open the nasal passages at the point of stricture. Many designs are made of wire, or include large loops, hooks or bead ends that are designed to engage the inside tip of the nose, press down on the floor of the nasal passage or spread the nasal passage vertically rather than laterally (U.S. Pat. Nos. 1,077,574; 2,515,756; Des. Pat. No. 325,439; U.S. Pat. Nos. 6,270,512; 6,863,066). Others include vertically wide strip-like members of spring metal or plastic (U.S. Pat. No. 6,238,411; US2006/0266367; DE 29718838; U.S. Pat. No. 6,238,433). One design (U.S. Pat. No. 6,238,411) combines adhesive strips secured to metal spring on the exterior of the nostrils while using another spring attached to the first that pushes open the nostrils from the inside; the device hangs down over the upper lip, and appears long enough to obstruct the mouth. Some appear to obstruct, rather than open the nasal passages (US2006/0266367; U.S. Pat. No. 3,710,799; DE 2978838), and others do not appear easy to clean or sanitize (U.S. Pat. Nos. 2,672,138; 3,710,799). For such reasons, few have made it into or lasted an appreciable length of time in commercial use.

There is thus an unmet need in the field for a truly universal, comfortable, reusable, unobtrusive, internal nasal passage dilation device that is easy for the user to insert, is effective and easy to clean and sanitize, is simple and inexpensive to manufacture, and comfortable enough to wear during sleep without internal pinching of the septum or overstretching of the nostrils.

THE INVENTION

Summary, Including Objects and Advantages

The inventive device comprises an internal nasal passage dilation device comprising a plastic nasal septum "clip" that includes a first pair of generally parallel arms to engage the median portion of the nasal septum, laterally cantilevered from which are a second pair of curved arms that flexibly function as springs to open the nostrils and keep them open. In addition, there is an open loop-shaped base member from which the septum-engaging arms extend. This loop serves as a grippable handle for insertion of the clip device in the nose.

In an alternate embodiment, the base loop member may extend laterally to engage the inside surface of the nostrils adjacent their external opening in order to spread them open. In addition, this base loop member may be angled "down" or/and curved with respect to the plane of the two septum-engaging arms in order to more nearly follow the natural shape of the upper lip where it meets the nasal passage openings.

In an important aspect of the inventive device, the outer cross-member of the base loop includes a notch that serves as a living hinge. This permits the device to be comfortable, in that the septum-engaging arms can flex open to accommodate various and differing widths of the septums of different users. In addition, it accommodates the fact that the septum generally widens or has a variable thickness as it extends up the nasal passage. The ends of the septum-engaging arms and the nasal passage-opening spring arms terminate in beads or flattened (in vertical cross section) pads to engage, respectively, the surface of the septum and the inner surface of the nostrils, so that the device is comfortable in use as inserted in the nasal passages.

This living hinge-enabled flexibility of the septum engaging arms and the spring flexibility of the nasal passage opening arms makes the inventive device universal. One size fits all, as the flexibility of the septum arms grip sufficiently to hold the device in place, even during activity, yet accommodate varying sizes of the nasal septum, from young to old, female to male. In addition, the spring action of the nostril-engaging arms accommodates various sizes of nasal passages. Due to the nature of springs, in that the more they are compressed together, the more outward force they exert, these nostril-engaging spring-action arms accommodate a wide range of obstructions (nasal passage restrictions), the narrower, the more opening force is applied.

The inventive breathing aid device can have a wide variety of configurations. For example, in the principal embodiment, the arms and base loop are round in cross-section. However, they may be oval, or ribbon-like with rounded edges, to spread the outward pressure of the arms against the septum and nostrils.

In another embodiment, the flexibility of the nostril-engaging arms can be supplemented with a wishbone hinge that spans between a medial portion of the septum-engaging arms and the nostril-engaging arms. Upon compression of the nostril-engaging arms, the recurved wishbone hinge acts as a compression spring resisting compression, and providing outward, and therefore nostril passageway opening function.

The material of construction is preferred to be plastic, and is preferably injection molded. A wide range of plastics may be used, including styrene polymers, olefin polymers such as polyethylene and polyproplyene, medical grade polymers, polyesters, polyurethane polymers, polycarbonates and the like mono-polymers, co-polymers and ter-polymers having the required rigidity, flexibility and spring-action resistance to compression. In addition, the device can be constructed of stainless steel, e.g., by stamping or wire-forming. In all cases it is preferred that the inventive breathing aid device be constructed of a material that is autoclavable, or otherwise sterilizable chemically, e.g., by immersion or swabbing with solutions containing one or more of dilute sodium hypochlorite, chlorhexidine, boric or benzoic acid, phenol, cetylpyridinium chloride, ethanol or isopropyl alcohol, other common antiseptics, or the like solutions.

With respect to view orientation for purposes of description of the inventive breathing aid device, it is generally planar, although, as noted above, in alternate embodiments the base loop may be angled or curved down from the plane of the septum-engaging arms, and the spring-action nostril engaging arms may be curved up from that plane. When viewed in plan view with the base loop closest to the viewer, the base loop may conveniently be described as located down with the living hinge section being outside the nasal septum, and the septum-engaging arms extending up or interior of the nasal passage. The direction extending interiorly of the nasal passages is considered the longitudinal axis of the device (front to back in plan view), and the cantilever branch of the nostril-expanding arms extend in the lateral (or "horizontal") direction (left and right in plan view). Similarly, when the device is stood up on its base, the arms may be considered to extend "vertically" or "up". These orientations and directions are for the purpose of aiding verbal description of a complex three-dimensional shape and are not meant as limiting of the variations in orientation or extent of the parts or elements of the device that will be evident to one skilled in the art in the implementation of the functional features and elements of the invention.

The inventive breathing aid device generally comprises a main breathing aid device body having first and second, longitudinally extending, spaced apart, nostril-expanding arms, each connected to, respectively, first and second longitudinally extending ("vertical"), septum compression rods or arms, first and second support framing (C-shaped and facing each other in plan view) joined by a main hinge, the support framing and hinge together forming a base member comprising an open loop from which the septum-engaging arms longitudinally ("vertically") extend. The first and second nostril-expanding arms (also called the curved arms) have a generally curved shape which is designed to conform generally to the interior surface of the human nostril, such that the first, or left curved arm is a mirror of the second, or right curved arm, with the interior of each curved arm facing directionally towards the other so that the curved arms are bowed outwardly from but generally parallel to the septum engaging arms or rods, and extend beyond the upper (inner) longitudinal terminal ends of the septum-engaging arms or rods.

The first and second curved nostril-expanding arms are each connected to a respective first and second septum compression or gripping arm or rod by means of a laterally or horizontally extending cross-bar attached at one end to the bottom end (longitudinally proximate end) of each curved arm and at the other end to a medial portion of the septum-engaging and gripping compression arm or rod. The longitudinally distal (inner) ends of each of the septum-engaging arms and the nostril-expanding arms terminate in a generally rounded, smoothed or curved/flared ends that are comfortable in use. These end segments may range in shape from rounded balls to pad-shaped to spread the pressure over a larger area so that there is no point-source discomfort to the user.

The proximal ends of the longitudinally extending (bottom ends of the vertical) septum-engaging compression arms or rods each connect to and are carried by a generally "C"-shaped support or base frame member, which together form as the user-grippable handle region of the device. The two C-shaped base members are mirrors of each other, that is they face each other, and are flexibly connected at the proximal (bottom) end by a living hinge. This hinge permits the left support/base frame, left septum-engaging arm/rod, and left nostril-expanding arm to move as a unit with respect to the corresponding, right, mirror image, support/base frame, septum-engaging arm/rod and nostril-expanding arm, the living hinge being the central pivot point for the two segments of the inventive breathing aid device. The inventive device is made of a resilient material which, when inserted in the nasal passages, maintains its shape and acts to urge the nostrils outwardly while compressingly gripping the septum without painful pressure or long term discomfort.

One skilled in the art will appreciate that the thickness of the living hinge (as seen in plan view of the device), may be appropriately sized, both in thickness (in the longitudinal direction as defined above) and in the dimension of the cross section of the base member structure) to provide enough flexibility to accommodate the variations in septum width yet provide compressive resistance so the nostrils will be maintained open yet the septum will not be painfully compressed. It should also be noted that the septum terminates at its outer end (at the nostril opening) in a transverse web, so that in horizontal cross section, the septum is an inverted "T" shape. Thus the living hinge permits the user to expand the septum-engaging arms during insertion so that the arms do not pinch the transverse web. Yet the hinge returns the mirrored C-shaped base to a normal closed position so the septum is retainingly gripped. That is, the living hinge acts as a compression spring, in that it must be compressed to open the two halves of the device so that the hinge urges them back to a closed, septum gripping position. At the same time, the nostril-engaging arms urge the nostrils outwardly. Thus, there are opposed spring actions in the inventive device, the living hinge urging the mirrored parts of the device close, while the outer arms urging the nostrils apart.

Accordingly, the inventive device overcomes the deficiencies of the prior art devices, such as those exemplary ones disclosed above, while opening the nasal passageways to promote easier breathing and minimize the incidence of snoring. Another important advantage of the inventive device is that the septum-engaging arms, being compressed together by the living hinge, serve to compress the nasal septum at the entrance of a human nose, thereby reducing the incidence of snoring caused by a deviated septum. The inventive device both compresses the septum while simultaneously expanding the nostrils, which results in an enlarged, more open breathing passageway, while not obstructing the passageway, and doing so in an unobtrusive manner. The inventive device easily fits and accommodates to a variety of different user's nose sizes. The central, living hinge provides the functionality of flexible opening for ease of insertion and removal without snagging on or hurting the septum web. The inventive device, buy means of the opposed spring action and curved shape of the nostril-engaging arms is universally functional for a wide range of sizes and ages of users.

The inventive breathing aid device body can also be described as comprising first and second nostril-expanding arms (the curved, spring-action arms), first and second nose compression rods (the septum-engaging arms), first and second support framing (the open base loop), and a main hinge (the living hinge), which device is placed at (manually inserted into) the entrance of a user's nose or nasal passageways to provide easier breathing and to decrease the incidence of snoring.

BRIEF DESCRIPTION OF THE DRAWINGS

The invention is described in more detail with reference to the drawings, in which.

DETAILED DESCRIPTION, INCLUDING THE BEST MODES OF CARRYING OUT THE INVENTION

The following detailed description illustrates the invention by way of example, not by way of limitation of the scope, equivalents or principles of the invention. This description will clearly enable one skilled in the art to make and use the invention, and describes several embodiments, adaptations, variations, alternatives and uses of the invention, including what is presently believed to be the best modes of carrying out the invention.

In this regard, the invention is illustrated in the several figures, and is of sufficient complexity that the many parts, interrelationships, and sub-combinations thereof simply cannot be fully illustrated in a single patent-type drawing. For clarity and conciseness, several of the drawings show in schematic, or omit, parts that are not essential in that drawing to a description of a particular feature, aspect or principle of the invention being disclosed. Thus, the best mode embodiment of one feature may be shown in one drawing, and the best mode of another feature will be called out in another drawing.

All publications, patents and applications cited in this specification are herein incorporated by reference as if each individual publication, patent or application had been expressly stated to be incorporated by reference.

Figures 1, 2:
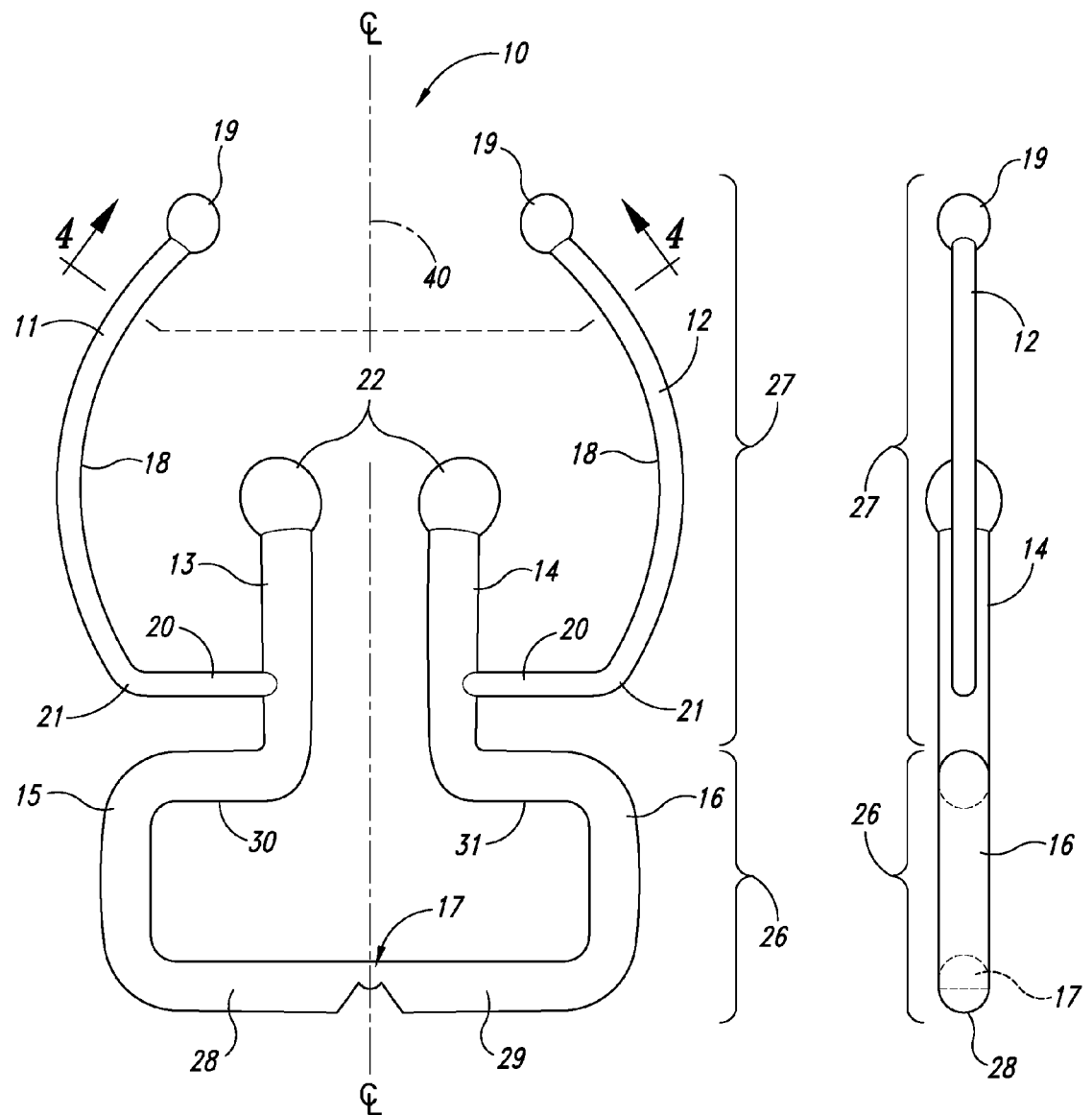
FIG. 1 is a plan view of a principal embodiment of the inventive breathing aid device.
FIG. 2 is a side elevation view of the embodiment of FIG. 1.
Figure 3:
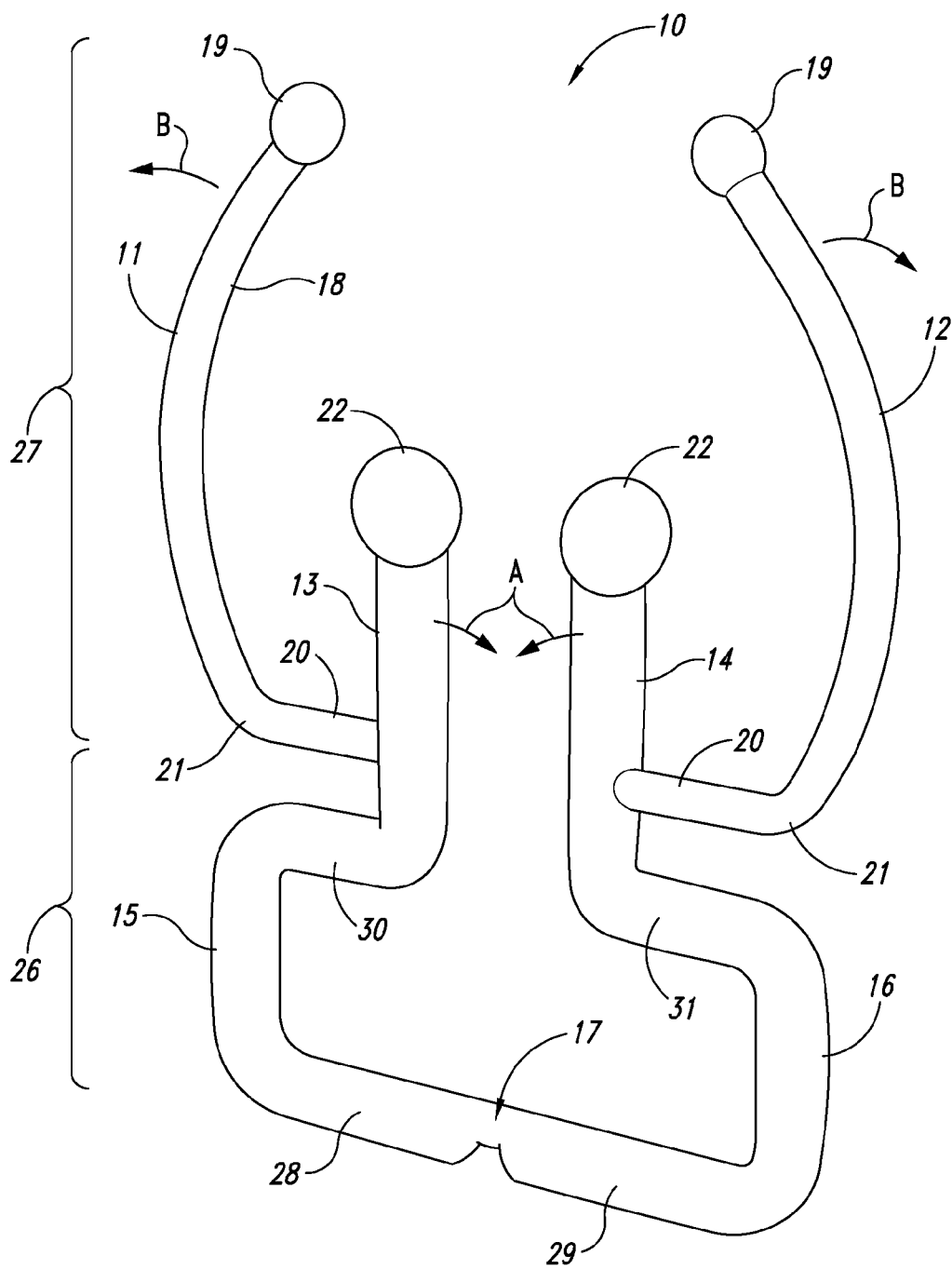
FIG. 3 is a ¾ isometric view of the embodiment of FIG. 1.

FIGS. 1, 2 and 3 show the inventive breathing aid device 10 as bilaterally symmetrical along a longitudinal axis Center Line 40, and comprises mirrored halves joined by a living hinge 17 in a base or frame section 26 to which are secured branched arm sections 27. Together the two mirror halves comprise a first, laterally curved nostril-expanding arm 11 and a second, mirror image laterally curved nostril-expanding arm 12. These arms have a generally curved shape which conforms generally to the interior surface contour of the human nostril (not shown), and are oriented with their concave contour 18 facing each other and spaced equidistant from the center line 40. Each arm 11, 12 terminates at its distal (interior) end in a rounded shape, such as a ball, a flared tip or foot, or a pad-shaped tip 19 (see also FIGS. 6 and 9).

The nostril-expanding arms 11, 12 are joined at their proximal ends 21 to the respective left and right septum-engaging and gripping arms 13, 14 by transverse (horizontal) cross-bars 20 that serve to cantilever the arms 11, 12 away from the arms 13, 14. The cross-bars 20 are joined to the arms 13, 14 medial of the joinder of those arms to the base 26 and their distal tips 22. As with the tips 19, the tips of the septum arms 13, 14 terminate in rounded, flared or pad-shaped ends, tips or feet.

The base member or frame 26 comprises generally mirror image C-shaped sections that face each other and are joined only at one point, the living hinge 17 located at the longitudinal center line 40 of its collective proximal cross-members 28, 29. Each half of the distal cross members 30, 31 of base 26 is joined to and carries the proximal end of the septum arms 13, 14, respectively. The septum arms are generally parallel and are spaced apart on the order of from about 0 (touching) to about 3 mm in the un-inserted (not-in-use) mode. That is, the living hinge urges the septum arms together to provide the gentle gripping needed to retain the inventive nasal clip assembly in place.

FIG. 3 also shows the counter-acting, cooperative spring action of the living hinge 17 and the flexible, spring-action arms 11, 12. Arrows A show the direction of compressive force by the living hinge on the septum-engaging and gripping arms 13, 14. Arrows B show the direction of expansive force by the spring-action resilience of the arms 11 and 12 to open the airway by expanding the nostrils.

Figure 4A:
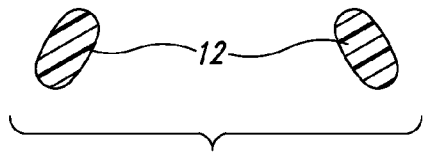
FIG. 4A is a section view of an alternate, oval and canted, embodiment of the nostril-expanding arms taken along the line 4-4 of FIG. 1.
Figure 4B:
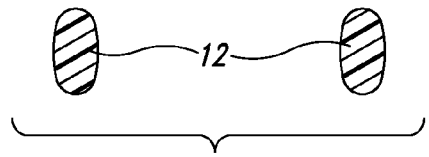
FIG. 4B is a section view of an alternate, oval and canted, embodiment of the nostril-expanding arms taken along the line 4-4 of FIG. 1 which is the embodiment of FIG. 4A inverted.
Figure 4C:
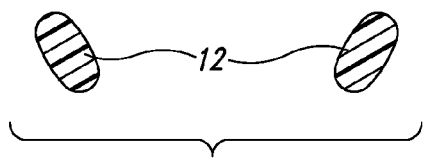
FIG. 4C is a section view of an alternate, oval but not canted, embodiment of the nostril-expanding arms taken along the line 4-4 of FIG. 1.

FIG. 4 is a series of cross sections of the arms 11, 12 showing additional embodiments in which the cross-section of the arms is generally flattened with chamfered edges or oval to provide more surface contact on the inner face of the nostrils. FIG. 4A shows the arms canted inwardly to follow the natural contour of the nostrils, being closer together near the bridge of the nose than the base, FIG. 4B shows them straight, that is parallel to the plane of the septum, which is orthogonal to the plane of the device of FIGS. 1-3. FIG. 4C shows them reverse canted. Note FIG. 4A also covers the embodiment of FIG. 4C, in that merely flipping the device over converts 4A to 4C. Stated another way, the canted orientation of the axis of the oval or flattened arm cross-sections, makes the device chiral (that is, it has a left-handed and a right-handed orientation). Since the 4C orientation could open the nostrils more, it means that the canted embodiment of the inventive device shown in FIGS. 4A/4C can fit a range of sizes of patient nostrils, e.g., women in 4A and men in 4C.

Figure 5:
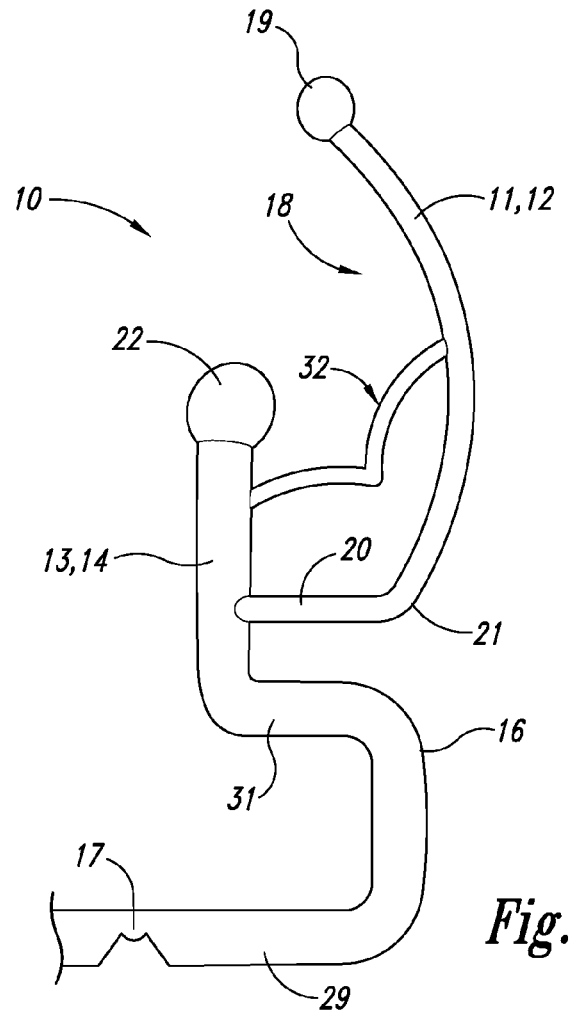
FIG. 5 is a plan view of an alternate embodiment of the device of FIGS. 1-3 employing an additional, wish-bone spring element.

FIG. 5 shows the use of a wishbone hinge 32 spanning between each septum arm 13, 14 and nostril arm 11, 12 to provide more outward force if needed. This device configuration may be particularly suitable for active users, e.g. athletes, and persons having collapsed nasal passages or highly deviated septums.

Figure 6:
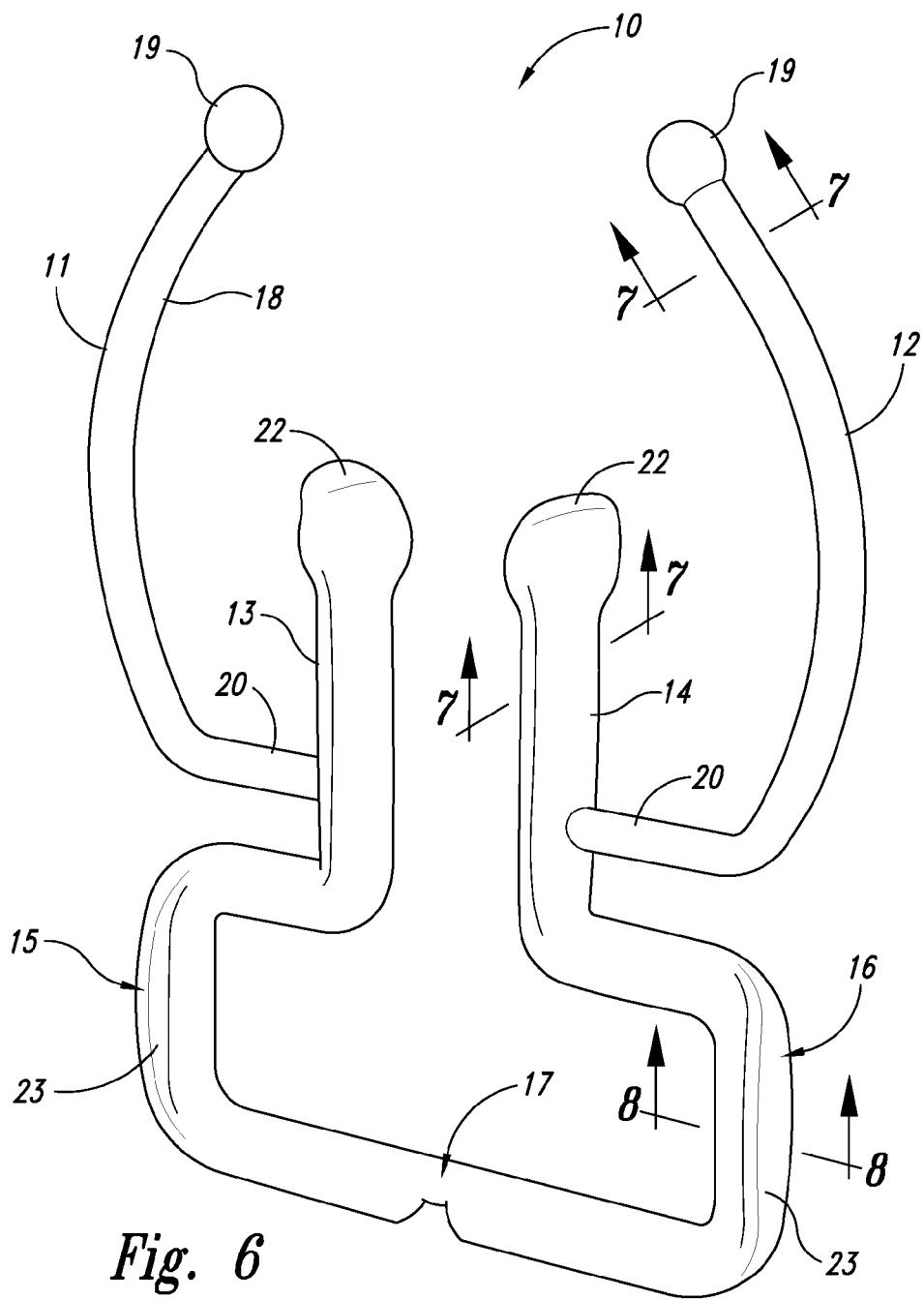
FIG. 6 is a ¾ isometric view of an alternate embodiment of the device of FIG. 3 in which the various cross-section configurations of the arms are flattened or contoured for comfort.
Figure 7:
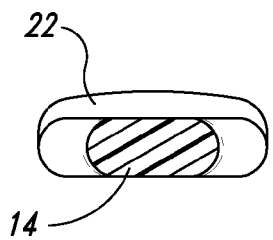
FIG. 7 is a cross-section of the septum and nostril arms of the embodiment of FIG. 6 taken along lines 7-7 of FIG. 6 also showing flattened, contoured pad-type tips.
Figure 8:
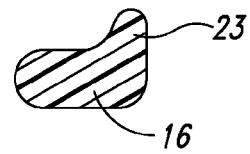
FIG. 8 is a cross section of the lateral segments of the base member taken along lines 8-8 of FIG. 6 showing the flared and flattened contour to provide better engagement and control of the nostril inner walls.

FIGS. 6-8 illustrate another embodiment in which the various arms and base longitudinal sections may be contoured with flattened, wider cross-sections that contact the skin of the nostrils and septum. Thus, FIG. 7 shows the septum arms 13, 14 may be flattened, and the tips 22 terminate in pads for better grip and comfort. Likewise, FIG. 8 shows the outer surface of the longitudinal base connector members 23 may be flared or enlarged to assist in opening the nostrils where they connect to facial tissue (the cheeks).

Figure 9:
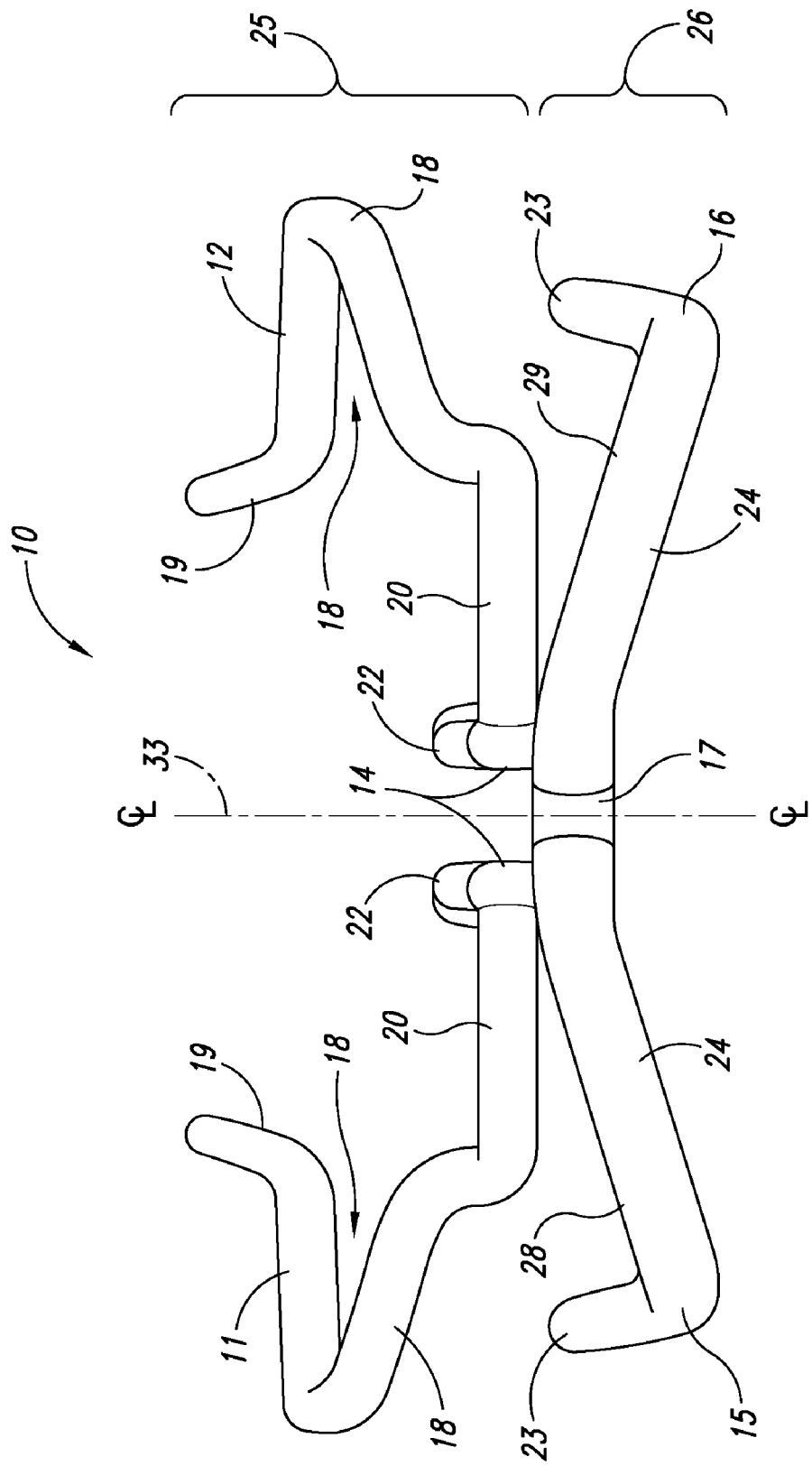
FIG. 9 is an end elevation of an alternate embodiment of the inventive breathing aid device in which the base member is angled to follow the contour of the face and the nostril-expanding arms are elevated.

FIG. 9 shows another embodiment in which the proximal elements 28, 29 of the base 26 are angled or canted downwardly 24 to follow the natural shape of the upper lip, with the living hinge being positioned at the philtrum, just below the septum. Also show, is the FIGS. 7 and 8 embodiment features of the enlarged webbing or flared section 23 and the pads 19 and 22. In addition the nostril-expanding bows 25 of the curved arms 11, 12 are shown as having a compound curve, with a portion of the curve elevated above the plane formed by the septum-engaging arms 13, 14. In this embodiment, the innovative breathing aid device is not restricted to the planar device shown in FIGS. 1-3, but rather is three dimensional, being angled laterally downwardly 24 in the base section 26, and elevated in the arm section 25. Thus, the inventive device has a Z dimension 33, the X dimension being the longitudinal dimension along center line 40 of FIG. 1, and the Y dimension being the lateral dimension (the direction of the cross-bars 20).

Note that the arms 11, 12 can also be curved down below the plane formed by the arms 13, 14, or have a compound curve in which portions of the arms 11, 12 extend both above and below the plane of arms 13, 14. These exemplary compound curves of arms 11, 12 also makes the device chiral such that the user can invert the device and insert it to provide a different expansion profile for the nostrils, depending on the needs of the individual.

Accordingly, the invention comprises a universal breathing aid device for compressing the nasal septum while dilating the nostrils to assist in maintaining the nasal passages open and to reduce the incidence of obstructed nasal passage-induced snoring, including: a clip assembly for engaging and gripping the nasal septum that is generally symmetric along a longitudinal center line, comprising: a base assembly having a pair of generally C-shaped members oriented facing each other in mirror symmetry along a longitudinal center line, said C-shaped members being joined only at their bottom segments by a living hinge, said joined C-shaped members together forming an open loop, and said living hinge being oriented to provide resistive force urging the open top segments of said C-shaped members toward each other; and a pair of septum-engaging arms, each joined to and extending longitudinally from a top segment of each C-shaped member, said septum-engaging arms being oriented parallel to and spaced from said center line a distance sufficient to grip and compress said septum upon closure force provided by said living hinge; a pair of curved, flexible, springy nostril-expanding arms, one each mounted to and oriented medially of the length of a septum-engaging arm, said nostril-expanding arms extending laterally from said septum-engaging arms, and the curve of said arms is oriented concave toward said center line; and said base member providing a handle for manual insertion of said clip in a user's nasal passage, said living hinge permitting said assembly to be sprung open to assist in insertion beyond the external web of said septum, and placed in said nasal passages with said septum-engaging arms gripping and gently compressing the septum, and the spring force of said nostril-expanding arms resisting compressive force of said nostrils while engaging the inner surfaces of said nostrils thereby to maintain them open.

Additionally, the distal ends of each of said septum-engaging and said nostril-expanding arms terminates in a rounded element selected from a ball, a pad and a flared foot in order to spread pressure and reduce discomfort. Further, at least a longitudinal portion of the cross-section of said septum-engaging arms is selected from round, oval and flattened with chamfered edges, and the long axis of said oval and said flattened cross-section being oriented generally parallel to the septum wall. And at least a portion of the longitudinal cross section of the cross-section of said nostril-expanding arms is selected from round, oval and flattened with chamfered edges, and the long axis of said oval and said flattened cross-section is oriented generally parallel to the inner wall of said nostril that it engages. In detail, said axis of said oval and flattened cross-sections of said nostril-expanding arms is selected from an orientation generally parallel to the plane of said septum and canted with respect to said septum plane, so that upon inversion of said device a somewhat different expansion contact is made with the interior surface of said nostrils. In one embodiment said breathing aid device structure is generally planar. In another embodiment, said C-shaped base members are angled downwardly with respect to said living hinge to follow the contour of the upper lip on each side of the philtrum. In the principal embodiment, said nostril-expanding arms are mounted at the ends of cross-bars extending laterally from said septum-engaging arms. In another embodiment, said nostril-expanding arms have a compound curve in at least a portion thereof, said curve extending both laterally outward from said center line and upward, downward or both upward and downward from a plane defined by said septum-engaging arms. Preferably, the material of construction of the inventive breathing aid device is selected from plastic and stainless steel. In still another embodiment the device includes an auxiliary resilient member disposed between said septum-engaging arm and said nostril-expanding arm to assist in expanding said nostril, which is preferably a compressive-type member that provides a force laterally outward from said center line, and in its most preferred implementation said compressive-type member is a wishbone hinge assembly.

INDUSTRIAL APPLICABILITY

It is clear that the inventive breathing aid device of this application has wide applicability in the field, namely to improve breathing for people having allergies, colds, deviated septums, and snoring problems. The inventive device clearly offers a combination of features that makes it universal and is unobtrusive as well as effective. Thus, the inventive breathing aid device has the clear potential of becoming adopted as the new standard for this field.

It should be understood that various modifications within the scope of this invention can be made by one of ordinary skill in the art without departing from the spirit thereof and without undue experimentation. For example, the particular arrangement and configuration of the septum arms and nostril arms can have a wide range of designs to provide the functionalities disclosed herein. The septum arms may also be configured with curves to accommodate various anatomical profiles of nasal cavities. This invention is therefore to be defined by the scope of the appended claims as broadly as the prior art will permit, and in view of the specification if need be, including a full range of current and future equivalents thereof.

The invention claimed is:

1. A universal breathing aid device for insertion into nasal passages of a user to compress the nasal septum while dilating the nostrils to assist in maintaining the nasal passages open and to reduce the incidence of obstructed nasal passage-induced snoring, comprising in operative combination:
   a) a clip assembly for engaging and gripping the nasal septum that is generally symmetric along a longitudinal center line, said longitudinal center line defining a proximal exterior end and a distal interior end with respect to said nasal passages when said clip assembly is inserted in the nasal passages comprising:
      i. a base assembly having a pair of generally C-shaped members oriented facing each other in mirror symmetry along said longitudinal center line, said C-shaped members having spaced apart bottom and top segments oriented normal to said longitudinal center line and extending generally horizon-tally, said bottom and top segments being joined by a connector segment spaced from and generally parallel to said longitudinal center line, said C-shaped members being joined only at their bottom segments by a living hinge, said living hinge being reduced in cross-section as compared to said bottom segments cross-section, said joined C-shaped members together forming an open loop, and said living hinge being oriented to provide resistive force urging the open top segments of said C-shaped members toward each other; and
      ii. a pair of septum-engaging arms, each joined to and extending longitudinally from and end of a top segment of each C-shaped member, said septum-engaging arms being oriented parallel to and spaced from said center line a distance sufficient to grip and compress said septum upon closure force provided by said living hinge;
   b) a pair of curved, flexible, springy nostril-expanding arms, one each mounted to and oriented medially of the length of a septum-engaging arm, each of said nostril-expanding arms having a base segment, said base segment having a first and a second end, said first end of said base segment being secured to said septum-engaging arm, and said base segment extending laterally from said septum-engaging arm to said second end, and a curved arm segment secured to said second end of said nostril-extending arm base segment, and said cureved arm segment extending distally to a free end that constitutes the distal interior end of said clip assembly, said curved arm segments are free and the curve of each is oriented concave toward said center line, and said nostril-expanding arms extend distally beyond the distal end of said septum-engaging arms; and
   c) said base assembly bottom segment providing a handle for manual insertion of said clip in a user's nasal passage, said living hinge permitting said assembly to be sprung open to assist in insertion beyond the external web of said septum, and placed in said nasal passages with said septum-engaging arms gripping and gently compressing the septum, and the spring force of said nostril-expanding arms reisting compressive force of said nostrils while engaging the inner surfaces of said nostrils thereby to maintain the nasal passages open without having structures that extend across and obstruct said nasal passages at said distal interior end.

2. A breathing aid device as in claim 1 wherein the distal ends of each of said septum-engaging and said nostril-expanding arms terminates in a rounded element selected from a ball, a pad and a flared foot in order to spread pressure and reduce discomfort.

3. A breathing aid device as in claim 2 wherein at least a longitudinal portion of the cross-section of said septum-engaging arms is selected from round, oval and flattened with chamfered edges, and the long axis of said oval and said flattened cross-section being configured to be oriented generally parallel to the septum wall.

4. A breathing aid device as in claim 2 wherein at least a portion of the longitudinal cross section of the cross-section of said nostril-expanding arms curved arm segments is selected from round, oval and flattened with chamfered edges, and the long axis of said oval and said flattened cross-section is configured to be oriented generally parallel to the inner wall of said nostril that it engages.

5. A breathing aid device as in claim 4 wherein said axis of said oval and flattened cross-sections of said nostril-expanding arms is selected from an orientation generally parallel to the plane of said septum, and an orientation canted with respect to said septum plane so that upon inversion of said device a somewhat different expansion contact is made with the interor surface of said nostrils.

6. A breathing aid device as in claim 1 wherein said device structure elements lie generally in a plane that includes said longitudinal center axis.

7. A breathing aid device as in claim 1 wherein said C-shaped base members are angled downwardly with respect to said living hinge, said downward angle being configured to follow the contour of the upper lip on each side of the philtrum.

8. A breathing aid device as in claim 1 wherein said C-shaped members are configured so that said connector segments engage the interor surface of said nostrils at the opening of said nostrils adjacent the upper lip.

9. A breathing aid device as in claim 8 wherein said nostril-expanding arms have a compound curve in at least a portion thereof, said curve extending both laterally outward from said center line and upward, downward or both upward and downward from a plane defined by said septum-engaging arms.

10. A breathing aid device as in claim 1 wherein the material of construction is selected from plastic and stainless steel.

11. A breathing aid device as in claim 1 which includes an auxiliary resilient member disposed between said septum-engaging arm and said nostril-expanding arm to assist in expanding said nostril.

12. A breathing aid device as in claim 11 wherein said auxiliary resilient member is a compressive-type member that provides a force laterally outward from said center line.

13. A breathing aid device as in claim 12 wherein said compressive-type member is a wishbone hinge assembly.

* * * * *